United States Patent [19]
Ishiguro et al.

[11] Patent Number: 5,871,441
[45] Date of Patent: Feb. 16, 1999

[54] ENDOSCOPE CAPABLE OF MANIPULATION SOON AFTER AUTOCLAVING

[75] Inventors: Tsutomu Ishiguro, Hachioji; Masaaki Nakazawa, Hino; Hisao Yabe, Hachioji; Hideo Ito, Akishima, all of Japan

[73] Assignee: Olympus Optical Co., Ltd., Tokyo, Japan

[21] Appl. No.: 577,321

[22] Filed: Dec. 22, 1995

[30] Foreign Application Priority Data

Dec. 27, 1994 [JP] Japan ................................ 6-326020

[51] Int. Cl.⁶ .................................................. A61B 1/04
[52] U.S. Cl. ........................................ 600/133; 600/159
[58] Field of Search ..................... 600/153, 155, 600/156, 159, 133, 121; 251/84, 128

[56] References Cited

U.S. PATENT DOCUMENTS

| | | | |
|---|---|---|---|
| 4,408,991 | 10/1983 | Engel | 433/30 |
| 4,592,344 | 6/1986 | Scheer | 128/13 |
| 5,299,561 | 4/1994 | Yoshimoto | 600/159 |
| 5,301,656 | 4/1994 | Negoro et al. | 600/159 X |
| 5,349,941 | 9/1994 | Hori | 128/4 |
| 5,433,725 | 7/1995 | Christian et al. | 606/207 |
| 5,545,121 | 8/1996 | Yabe et al. | 600/121 |
| 5,584,796 | 12/1996 | Cohen | 600/201 |

FOREIGN PATENT DOCUMENTS

| | | |
|---|---|---|
| 59-211424 | 11/1984 | Japan . |
| 2-121002 | 10/1990 | Japan . |

*Primary Examiner*—Beverly M. Flanagan
*Attorney, Agent, or Firm*—Armstrong, Westerman, Hattori, McLeland & Naughton

[57] ABSTRACT

An endoscope has a channel switching device for use in switching over a suction channel. The channel switching device consists broadly of a cylinder unit and valve unit. The valve unit can be disassembled into three component parts; a button assembly, piston assembly, and mount assembly. The button assembly has a cap, which is made of a rigid resin such as polyether ketone (PEEK) or polysulfone (PSU), as the uppermost part thereof. Since the cap is made of a rigid resin durable to autoclaving; such as, PSU or PEEK, the valve unit will not be damaged due to autoclaving. Even when the autoclaved valve unit is put to use though it is not yet cooled down, an operator will not perceive heat very much but can manipulate the endoscope as he/she intends.

9 Claims, 17 Drawing Sheets

ENDOSCOPE CAPABLE OF MANIPULATION SOON AFTER AUTOCLAVING

BACKGROUND OF THE INVENTION

1. Field of the Invention

The present invention relates to an endoscope having a channel switching device for switching the communicating states of a plurality of kinds of channels lying through an insertional part for the purpose of such functions as aeration, perfusion, and suction.

2. Description of the Related Art

Generally, in addition to illumination optical fibers, an imaging optical system, and observation optical fibers, many members such as a forceps channel tube that is also used for a suction channel, an aeration channel tube, and a perfusion channel tube are incorporated in an insertional part of an endoscope. For implementing various functions in an endoscope, it is necessary to insert various members in an insertional part of the endoscope. This poses a problem that the insertional part becomes larger in diameter.

Proposed in, for example, Japanese Unexamined Utility Model Publication No. 2-121002 is an endoscope whose insertional part is made thinner by placing a channel switching device in an operation unit.

As shown in FIG. 29, in a channel switching device 200 disclosed in the Japanese Unexamined Utility Model Publication No. 2-121002, a push button 202 formed on the top of a piston 201 is pushed in order to switch channels. The push button 202 is firmly screwed down by means of a male-threaded section 203 of the push button 202 and a female-threaded section 204 in the upper part of the piston 201.

Generally, the foregoing channel switching device included in an endoscope comprises a cylinder unit formed in an insertional part of the endoscope and a valve unit attached to the cylinder unit.

For reusing the endoscope, at least the endoscope and valve unit must be disinfected.

For effective disinfection using a disinfectant solution, it is necessary to expose all the ins and outs of the valve unit to the disinfectant solution. The valve unit is therefore usually detached from the endoscope and then disinfected.

However, since the valve unit has a relatively complex structure, the work of brushing or swinging the valve unit in the disinfectant solution is required to expose all the ins and outs of the valve unit to the disinfectant solution. The disinfection work using a disinfectant solution is therefore time-consuming. Besides, special care must be taken for fear the disinfectant solution be splashed on a human body during the disinfection work.

By contrast, autoclaving is a sterilizing means using hot steam. Since steam penetrates all the ins and outs of a member having a complex structure, the valve unit can be sterilized reliably. Moreover, sterilization can be completed safely and easily for a short period of time. It is therefore preferred that the valve unit be autoclaved.

However, since the known valve unit is not made of a material that is durable to autoclaving, when the valve unit is autoclaved, component parts constituting the valve unit may be damaged.

Moreover, during autoclaving, the valve unit is exposed to a hot steam environment of about 120° to 135° C. The temperature of the valve unit itself reaches about 120° to 135° C. After being autoclaved, when the valve unit is used for endoscopic examination, as long as the valve unit is cooled down to around the room temperature of an endoscopic examination room, a heat-related problem will not arise for an operator. For increasing the patient throughput of endoscopic examination, it is required not to wait until the valve unit is cooled down to the room temperature but to use the valve unit in a heated state in which the temperature of the valve unit is still higher than the room temperature. In this case, depending on the temperature of the valve unit, an operator cannot manipulate the endoscope as he/she intends. In particular, when a metallic member constitutes an outer surface of a valve, there arises a problem that an operator is likely to perceive heat and be hindered from manipulating an endoscope freely.

OBJECT AND SUMMARY OF THE INVENTION

An object of the present invention is to provide an endoscope that is durable to autoclaving and that even when disinfected by autoclaving, can be manipulated soon after the autoclaving.

An endoscope of the present invention has channels incorporated in an insertional part, and a channel switching device placed in the middle of the channels for switching the communicating states of the channels. The channel switching device comprises a cylinder unit and a valve unit freely detachable from the cylinder unit. All the members constituting the valve unit are made of a material durable to autoclaving. The valve unit has an outer surface made of a material other than a metal when mounted on the cylinder unit.

Other features and advantages of the present invention will be fully apparent from the description below.

BRIEF DESCRIPTION OF THE DRAWINGS

FIG. 1 is a sectional view showing the structure of a channel switching device;

FIG. 2 shows the configuration of an endoscope having the channel switching device shown in FIG. 1;

FIG. 3 is a sectional view of an endoscope symbolically showing a channel to be switched over by the channel switching device shown in FIG. 1;

FIG. 4 is a sectional view showing the structure of a button assembly on an 4—4 cross section of FIG. 1;

FIG. 5 is a side view showing the structure of a piston shown in FIG. 1;

FIG. 6 is a sectional view showing a 6—6 cross section of FIG. 5;

FIG. 7 is a sectional view showing a 7—7 cross section of FIG. 5;

FIG. 8 is a sectional view showing an 8—8 cross section of FIG. 1;

FIG. 9 is a sectional view showing a 9—9 cross section of FIG. 1;

FIG. 10 is a sectional view showing a first variant of juts shown in FIG. 9;

FIG. 11 is a sectional view showing a second variant of the juts shown in FIG. 9;

FIG. 12 is a side view showing the structure of a stopper shown in FIG. 8;

FIG. 13 is a side view showing the structure of a first variant of the stopper shown in FIG. 8;

FIG. 14 is a side view showing the structure of a second variant of the stopper shown in FIG. 8;

FIG. 15 is a sectional view showing an 15—15 cross section of FIG. 8;

FIG. 16 shows the appearance of a cylinder body in FIG. 1 viewed from above;

FIG. 17 is a development diagram in which a piston passage in the cylinder body shown in FIG. 16 is developed;

FIG. 18 is a first explanatory diagram on assembling for explaining construction of the valve unit shown in FIG. 1;

FIG. 19 is a second explanatory diagram on assembling for explaining construction of the valve unit shown in FIG. 1;

FIG. 20 is a sectional view showing a 20—20 cross section of FIG. 19;

FIG. 21 is a first explanatory diagram on an operation for explaining pushing of the valve unit shown in FIG. 1;

FIG. 22 is a second explanatory diagram on an operation for explaining pushing of the valve unit shown in FIG. 1;

FIG. 23 is a third explanatory diagram on an operation for explaining pushing of the valve unit shown in FIG. 1;

FIG. 24 is a first explanatory diagram for explaining the operation of a button assembly of the valve unit shown in FIG. 1 induced by a movement of a finger;

FIG. 25 is a second explanatory diagram for explaining the operation of the button assembly of the valve unit shown in FIG. 1 induced by a movement of a finger;

FIG. 26 is a sectional view showing the structure of a channel switching device;

FIG. 27 is a sectional view showing a V—V cross section of FIG. 26;

FIG. 28 is an enlarged sectional view showing the structure of a variant of FIG. 26.

DETAILED DESCRIPTION OF THE PREFERRED EMBODIMENTS

Figure 2:
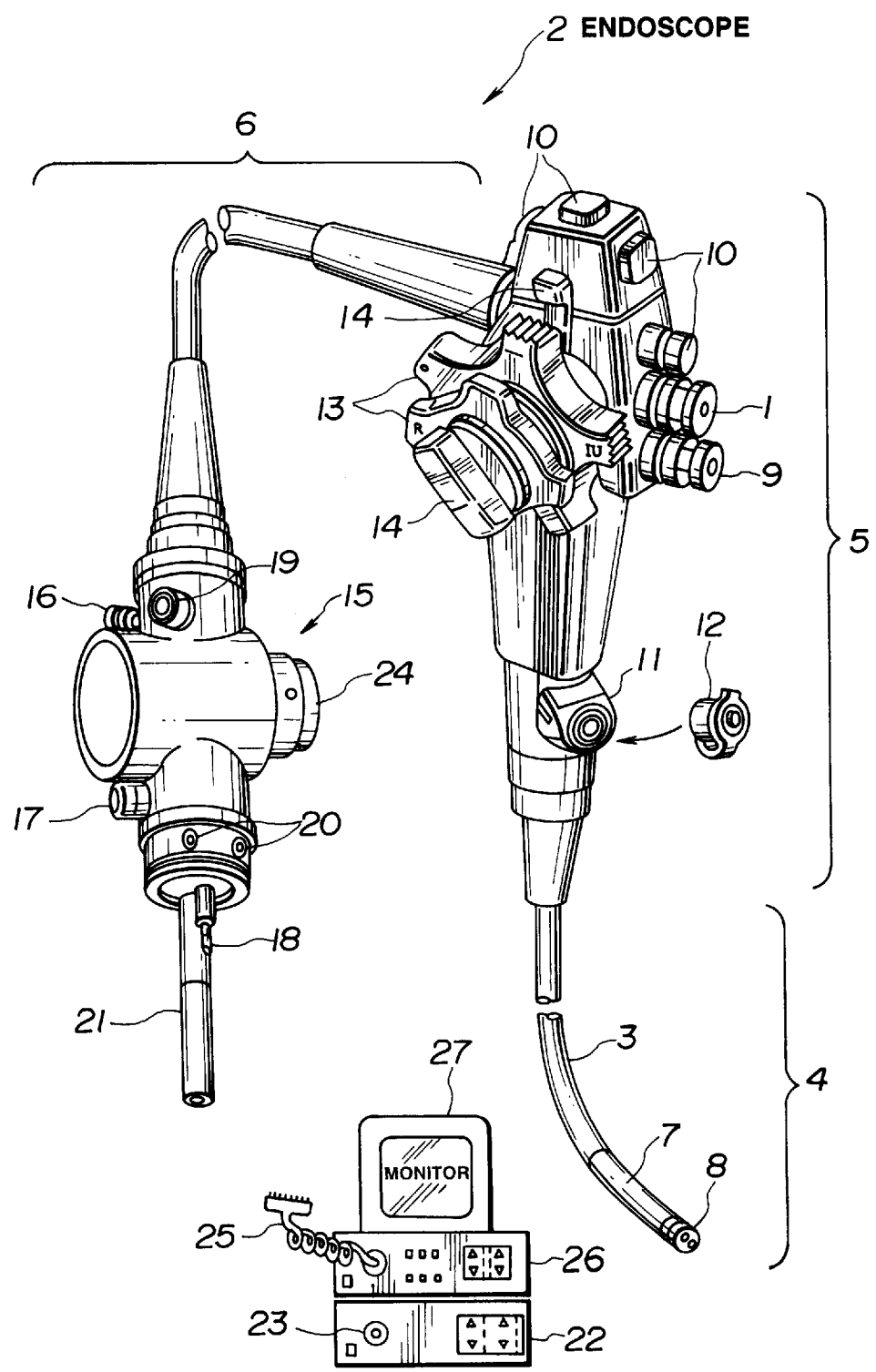

As shown in FIG. 2, an endoscope 2 of this embodiment comprises an insertional part 4 having a flexible tube 3 and others, an operation unit 5 formed at the proximal end of the insertional part 4, and a universal cord 6 extending from the operation unit 5.

The insertional part 4 is coated with a resin such as polyurethane, and has a bending section 7, which is coated with a soft elastic body such as silicon rubber, latex, or the like, as a distal portion thereof. A distal rigid section 8 is formed at the tip of the bending section 7. The distal rigid section 8 has an observation optical system, imaging device, illumination optical system, aeration/perfusion nozzle, and forceps outlet, which are not shown.

A channel switching device 1 for use in switching over a suction channel that will be described later, an aeration/perfusion valve 9 to be manipulated for aeration or perfusion, remote switches 10 for use in processing video signals supplied from an imaging device (not shown) are mounted on the operation unit 5. A forceps opening 11 communicating with a suction channel that will be described later is formed in the operation unit 5 on the side of the insertional part 4. A forceps plug 12 can be fitted into the forceps opening 11. When forceps are not inserted through the forceps opening 11, the forceps plug 12 is fitted into the forceps opening 11 in order to seal up the forceps opening 11.

An angling knob 13 made of a rigid resin such as polypropylene (hereinafter PP), polyamide (hereinafter PA), polyacetal (hereinafter POM), polyethylene (hereinafter PE), polybutylene terephthalate (hereinafter PBT), polyphenylene sulfide (hereinafter PPS), polystyrene (hereinafter PS), styrene-acrylonitrile (hereinafter SAN), acrylonitrile-butadien-styrene (hereinafter ABS), acrylic (hereinafter PMMA), polycarbonate (hereinafter PC), polyphenylene oxide (hereinafter modified PPO), polyether ketone (hereinafter PEEK), polysulfone (hereinafter PSU), or polyethylene terephthalate (hereinafter PET) is mounted on the operation unit 5. By manipulating the angling knob 13, the bending section 7 can be angled laterally and vertically. An FE lever 14 made of a rigid resin and used to retain or release the bending section 7 at or from an angle fixed state is also mounted on the operation unit 5.

The universal cord 6 is coated with a resin such as polyurethane. A connector 15 made of a rigid resin such as PP, PA, POM, PE, PBT, PPS, PS, SAN, ABS, PMMA, PC, modified PPO, PSU, PEEK, or PET is attached to the tip of the universal cord 6.

A switch terminal 16 for returning a radio-frequency (hereinafter RF) leakage current to a cautery power supply, a metallic perfusion base 17 for use in connecting a perfusion tank, which is not shown, for supplying water, a metallic aeration tube 18 used for aeration, a suction base 19 for use in connecting a suction pump that is not shown, and electrical contacts 20 that are electrically connected to an imaging device, which is not shown, incorporated in the distal rigid section 8 are mounted on the connector 15.

The connector 15 has a light guide end 21. The light guide end 21 is coupled with a connector receptor 23 on a light source unit 22, whereby illumination light propagates through a light guide that is not shown, and is then emitted through an illumination optical system incorporated in the rigid distal section 8.

An electrical connector 24 is mounted on the lateral side of the connector 15. A connection cord 25 is coupled with the electrical connector 24 in order to connect the endoscope to a video processor 26, whereby an electric signal supplied from the imaging device (not shown) is visualized as an image on a monitor 27.

Figure 3:
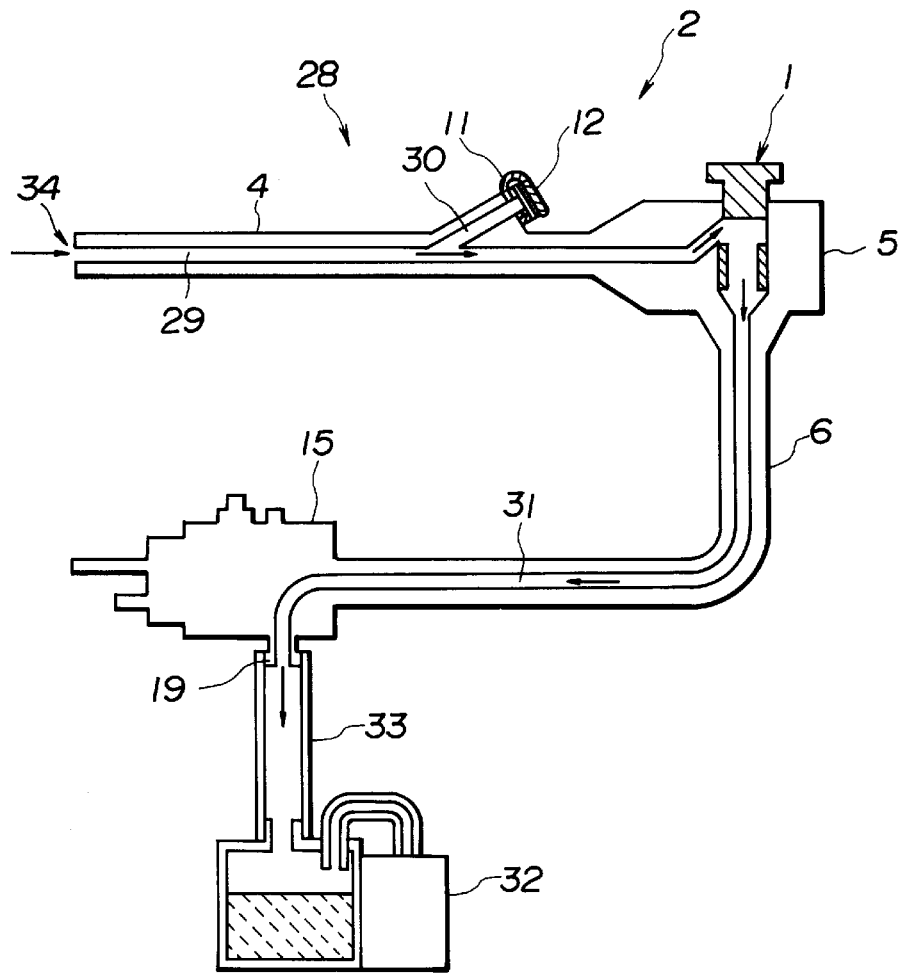

A suction channel 28 in the endoscope, which is switched over by the channel switching device 1, is, as shown in FIG. 3, composed of an upstream suction channel 29 lying through the insertional part 4 and communicating with a suction opening 34 formed at the tip of the insertional part 4, a bifurcate channel 30 communicating with the forceps opening 11 formed in the operation unit 5, a downstream suction channel 31 lying through the universal cord 6, the suction base 19 mounted on the connector 15 and formed at the end of the downstream suction channel 31, and a suction tube 33 to be coupled with the suction base 19 for linking a suction pump 32 and the suction base 19. The channel switching device 1 is interposed between the upstream suction channel 29 and downstream suction channel 31, and switches from a suction state to a non-suction state or vice versa.

Figure 1:
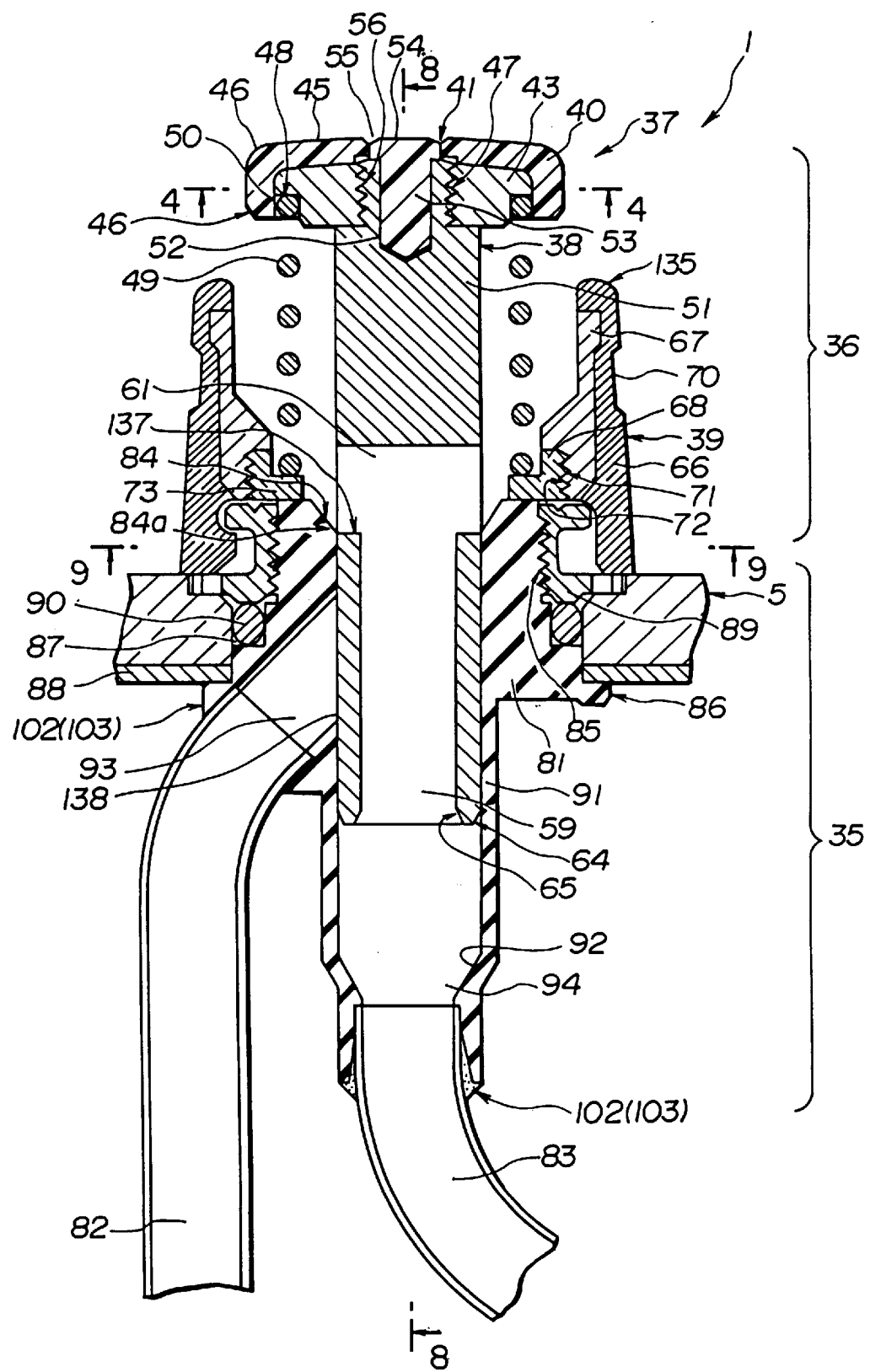
FIGS. 1 to 25 relate to the first embodiment of the present invention.

As shown in FIG. 1, the channel switching device 1 consists broadly of a cylinder unit 35 and valve unit 36. The valve unit 36 can be disassembled into three component parts; a button assembly 37, piston assembly 38, and mount assembly 39.

Since the valve unit 36 can be disassembled into three component parts, every part of the valve unit 36 can be cleaned readily and reliably during a cleaning operation.

The button assembly 37, piston assembly 38, and mount assembly 39 will be described below.

The button assembly 37 has a cap 40 made of a rigid resin such as PSU or PEEK as the top thereof. A center hole 41 penetrating through the cap 40 is bored in the center of the cap 40.

Figure 4:
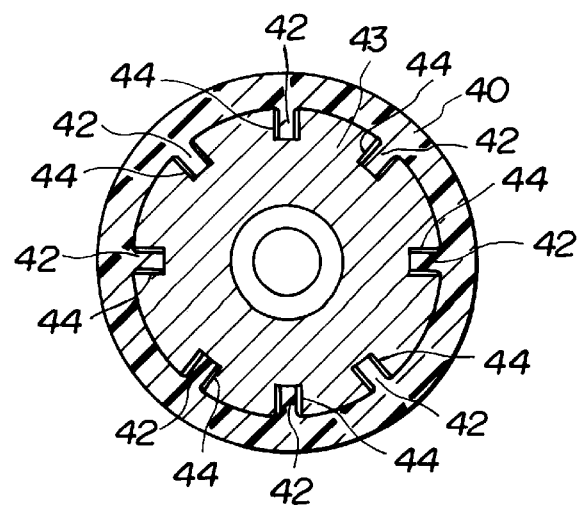

The cap 40 has, as shown in FIG. 4 which is an A—A cross section of FIG. 1, a circular cross section, and has a plurality of ribs 42 formed along an inner circumference. In this embodiment, eight ribs 42 are located equidistantly along the circumference of the cap. However, the ribs 42 need not be positioned equidistantly along the circumference. The number of ribs is not limited to eight but may be larger or smaller than eight.

A metallic member 43, made of a metal such as SUS, brass, or aluminum, is mounted inside of the button assembly 37. Eight ditches 44 are bored equidistantly along the outer circumference of the metallic member 43 in relation to the ribs 42. Similarly to the ribs 42, as long as the ditches 44 are formed in relation to the ribs, the ditches 44 need not be positioned equidistantly along the circumference. The number of the ditches 44 is not limited to eight but may be larger or smaller than eight.

The ribs 42 on the cap 40 are fitted into the ditches 44 in the metallic member 43, thus preventing rotations of the cap 40 and metallic member 43 and positioning them. Moreover, the cap 40 and metallic member 43 are attached firmly to each other using an adhesive in such a way that there is no clearance between them.

Thus, the ribs 42 on the cap 40 are fitted into the ditches 44 in the metallic member 43, and the cap 40 and metallic member 43 are firmly attached to each other with no clearance between them. Occurrence of a bio-film can therefore be prevented.

Returning to FIG. 1, it is seen that the top of the cap 40 has a rounded surface 45. The upper and lower circumferential parts of the cap 40 each have a rounded chamfered section 46.

The button assembly 37 usually has a black appearance. The color is not limited to black but may be any other one. For example, red, which is a widely-adopted index of suction, will do.

A female thread 47, which is a right-hand thread, is formed in the center of the metallic member 43. When the cap 40 and metallic member 43 are firmly attached to each other, the female thread 47 and center hole 41 communicate with each other.

A spring mounting section 48 is formed along the whole outer circumference of the bottom of the metallic member 43. A spring 49, which is a constraining means working on the channel switching device 1, is firmly attached to the cap 40 and spring mounting section 48 using an adhesive 50.

In this embodiment, the spring 49 is a right-hand coil spring. Alternatively, the spring 49 may be a left-hand coil spring.

When the spring 49 is blackened by performing finishing such as painting or plating, the inconsistency in appearance with other component parts is eliminated. In this embodiment, the spring 49 is blackened by performing finishing such as painting or plating. Alternatively, the spring 49 may have the metallic base bared.

The piston assembly 38 has a piston 51. The piston 51 has a circular cross section and is made of a metal such as stainless steel, aluminum, steel, or brass. An index mounting hole 52 having a circular cross section is bored in the upper part of the piston 51. An index 53 having a circular cross section is firmly attached to the mounting hole 52 using an adhesive. The index mounting hole 52 and index 53 must have the same cross sectional shape. The cross sectional shape may not be circular but may be a polygon such as a hexagon, square, or triangle. A gap between the index mounting hole 52 and index 53 is filled with an adhesive without any clearance. A bubble of the adhesive will not remain inside. Since the gap between the index mounting hole 52 and index 53 is filled with the adhesive without any clearance, occurrence of a bio-film between the index mounting hole 52 and index 53 can be prevented.

The index 53 is made of a rigid resin such as PSU or PEEK. The index 53 has a different color from an aeration/perfusion index formed at the apex of an aeration/perfusion valve 9, whereby the index 53 is distinguished from the aeration/perfusion valve 9. The preferred color of the index 53 is generally red.

Since the index 53 has a different color from the aeration/perfusion index, the aeration/perfusion valve 9 and suction channel switching device 1 can be distinguished from each other readily. This contributes to the improvement of operability.

The top of the index 53 is an index top end 54 which has a circular cross section having an outer diameter equal to or smaller than the diameter of the center hole 41 bored in the center of the cap 40. A chamfered section 55 is formed along the whole outer circumference of the uppermost part of the index 53. A male thread 56, which is a right-hand thread, is formed on the upper part of the piston 51.

Figure 5:
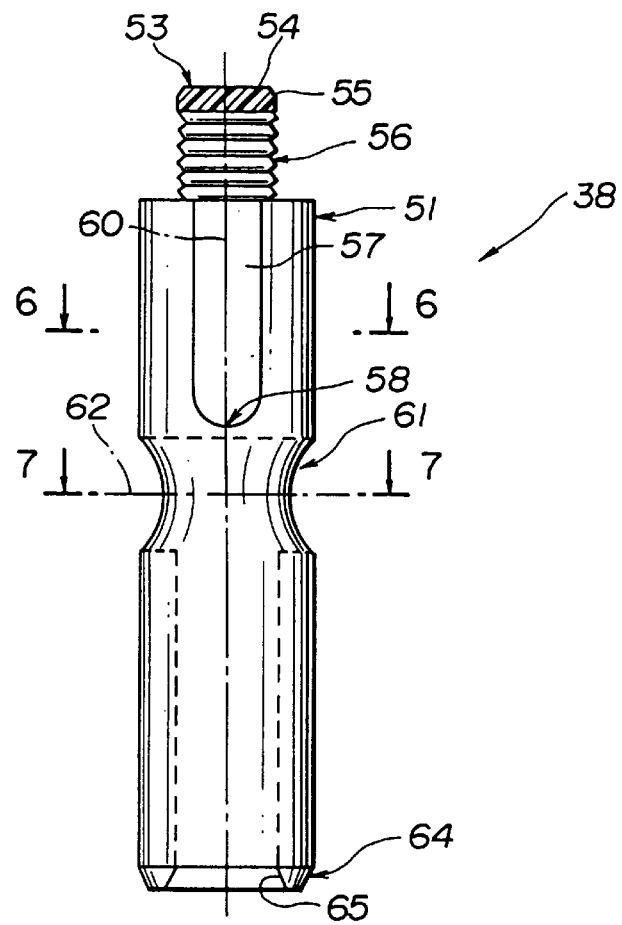
Figure 6:
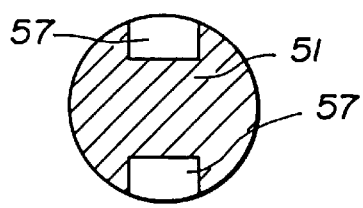

Two stoppage ditches 57 are, as shown in the FIG. 5 side view of the piston 51 and the FIG. 6 cross section along the line B—B of FIG. 5, formed at opposite positions along the circumference of the piston from the top end of the lateral side of the piston 51 to about the center thereof. The lower ends of the stoppage ditches 57 are rounded surfaces 58.

Figure 7:
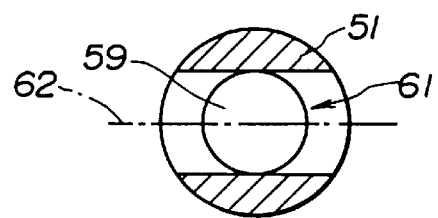

A vertical channel 59 having a circular cross section and lying along the axis of the piston 51 is, as shown in the FIG. 7 cross section along the line Q—Q of FIG. 5, formed from the lower end of the pixel 51 toward the center of the cylinder unit.

An orthogonal channel 61, having a circular cross section and being orthogonal to a center axis 60 in the longitudinal direction of the piston 51 shown in FIG. 5, is penetrating through the piston 51 laterally in the center of the center of the piston 51. In this embodiment, the inner diameter of the orthogonal channel 61 is equal to that of the vertical channel 59. The upper end of the vertical channel 59 is leveled with an orthogonal channel center line 62 that is a center line of the orthogonal channel 61. As shown in the FIG. 8 cross section along line 8—8 of FIG. 1, a junction 63 between the vertical channel 59 and orthogonal channel 61 is not stepped. The junction 63 has no cul-de-sac structure.

Since the junction 63 between the vertical channel 59 and orthogonal channel 61 is not stepped, cleaning can be achieved readily. Since the junction 63 has no cul-de-sac structure, the orthogonal channel 61 can be cleaned readily by inserting a cleaning brush to the orthogonal channel 61 during cleaning. Likewise, the vertical channel 59 can be cleaned readily by inserting a cleaning brush to the vertical channel 59. Moreover, the junction 63 can be cleaned readily and reliably. Since the orthogonal channel 61 in the piston 51 is penetrating through the piston 51 in a direction orthogonal to the center axis of the piston 51, a cleaning brush can be inserted to the orthogonal channel 61 readily during cleaning of the piston 51. This contributes to the improvement in cleaning efficiency.

Returning to FIG. 1, it is seen that a slope 64 is formed along the whole outer circumference of the lower end of the piston 51. The lower end of the vertical channel 57 has a chamfered section 65.

The mount assembly 39 comprises a mounting rubber 66 made of an elastic body such as silicon rubber, latex, thermoplastic elastomer, or vinyl chloride, a metallic insert 67 made of a metal such as SUS, aluminum, or brass and molded as an insert using the mounting rubber, and a piston positioning member 68 made of a metal such as an aluminum alloy, SUS, brass, or steel.

Figure 9:
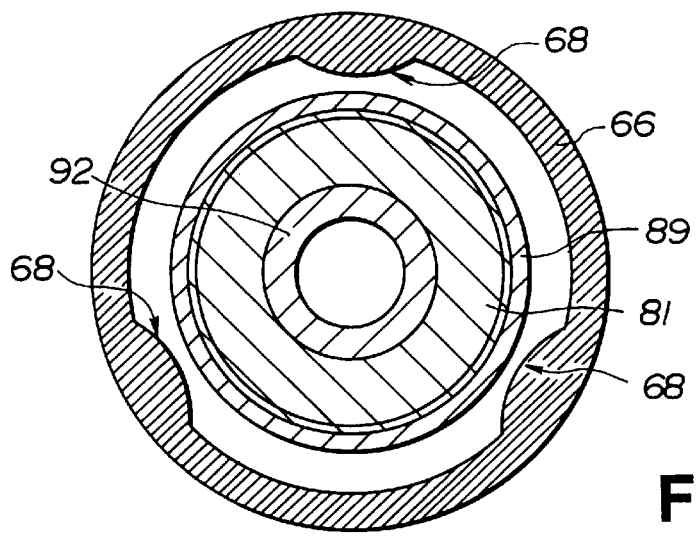

The mounting rubber 66 has, as shown in the FIG. 9 cross section along line C—C of FIG. 1, three juts 69 formed equidistantly along the inner circumference of the lower part thereof.

Since the juts 69 are separated from one another, dirt can be removed readily during cleaning of the juts. The cleaning efficiency of the mounting rubber 66 therefore improves.

Figure 10:
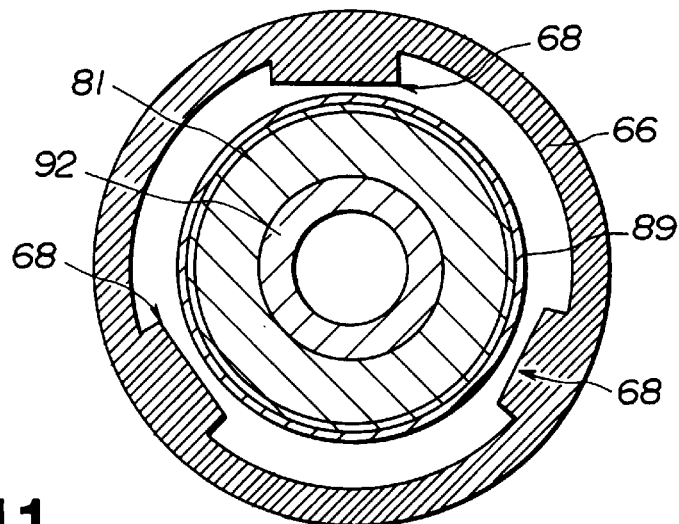
Figure 11:
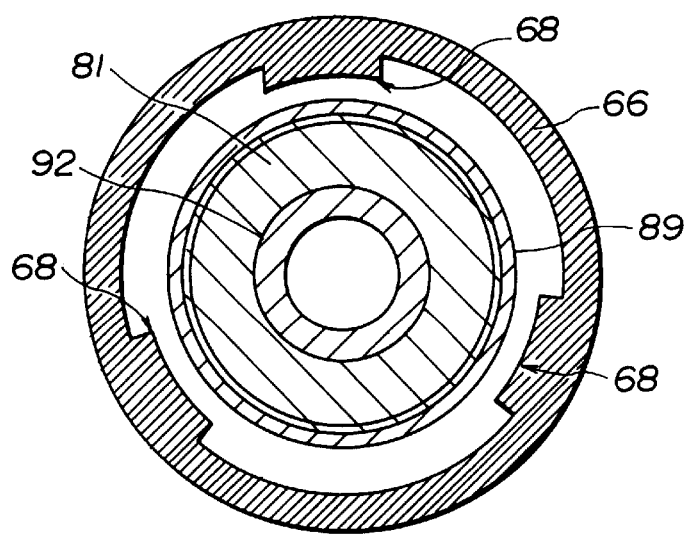

In this embodiment, the cross sections of the juts 69 have a circumferentially bossy shape. The cross-sectional shape is not limited to the circumferentially bossy shape but may be a rectangle as shown in FIG. 10 (corresponding to the C—C cross section of FIG. 1) illustrating a first variant of the juts, or a circle that is, as shown in FIG. 11 illustrating a second variant of the juts (corresponding to the C—C cross section of FIG. 1), coaxial to the inner circumference of the mounting rubber. As long as a plurality of juts 69 are located mutually separately along the inner circumference of the lower part of the mounting rubber 66, the number of the juts 69 is not limited to three. In this embodiment the mounting rubber 66 is blackened. Alternatively, the color of the mounting rubber 66 may be other than black, for example, red, blue, or yellow. In this case, the color of the mounting rubber 66 may be different from the color of a mounting rubber, which is not shown, of the aeration/perfusion valve 9. That is to say, when the color of the mounting rubber 66 is made different between the aeration/perfusion valve 9 and suction channel switching device 1, the aeration/perfusion valve 9 and suction channel switching device 1 can be distinguished from each other readily.

Returning to FIG. 1, it is seen that a gripping ditch 70 is formed along the whole outer circumference of the mounting rubber 66 on the lateral side thereof. For gripping the valve unit 36, since fingers are caught in the gripping ditch 70, gripping is achieved readily. The gripping ditch 70 is rather shallow for the width. Dirt therefore hardly sticks on the gripping ditch. Even if dirt sticks, cleaning can be achieved readily.

A female thread 71 for use in securing the piston positioning member 68 is formed in the lower part of the insert 67. A male thread 72 is formed along the outer circumference of the piston positioning member 68. The female thread 71 and male thread 72 are mated up and an adhesive is applied to the mated threads, whereby the piston positioning member 68 is fixed to the insert 67.

Figure 8:
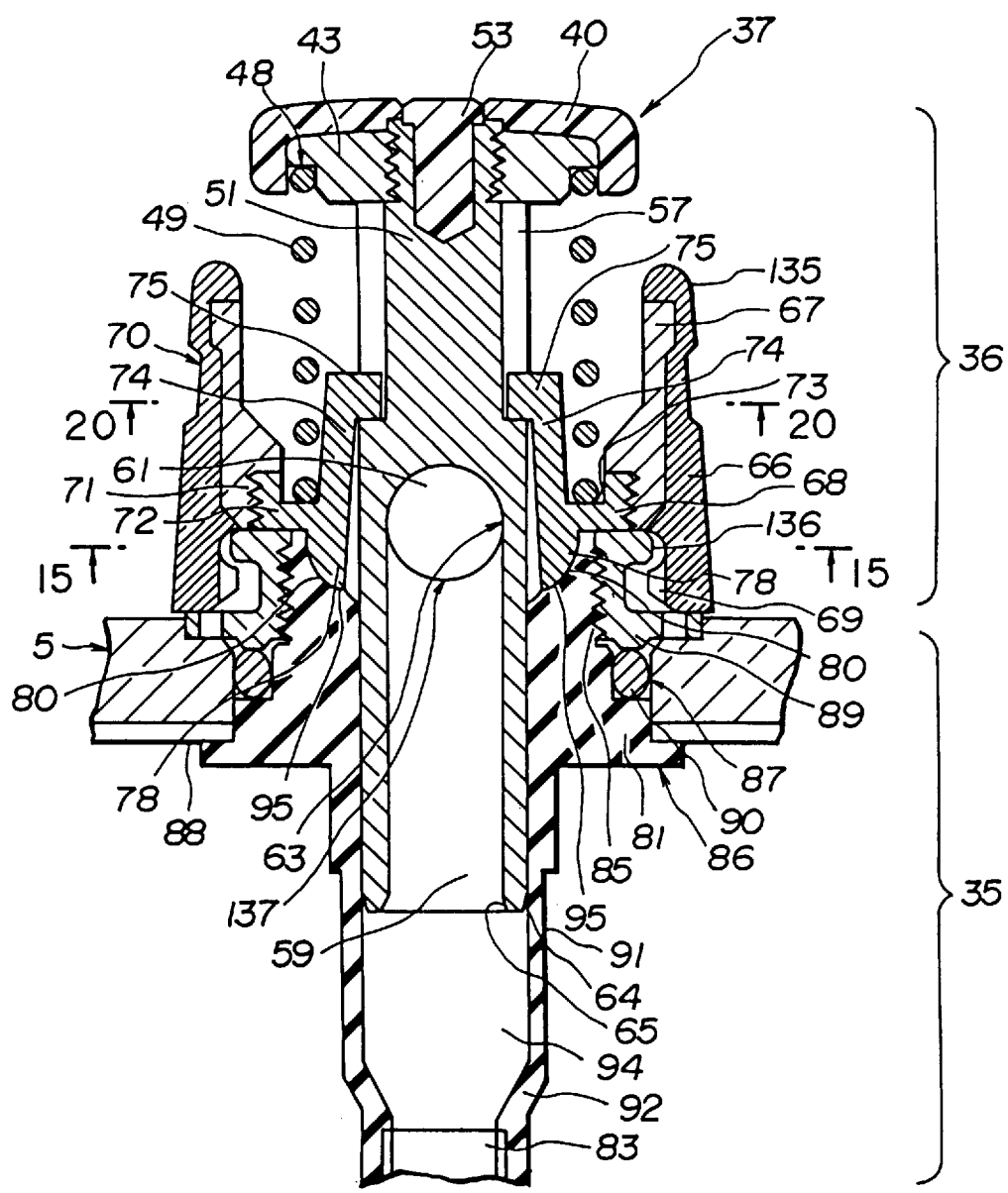

The piston positioning member 68 is made of a metal such as SUS, aluminum, brass, or steel, and has, as shown in the FIG. 8 cross section along line 8—8 of FIG. 1, a base 73 having a circular cross section and two pillars 74 extending upward from the base 73 at opposite positions. Stoppers 75 are formed at the upper ends of the two pillars 74 in such a way that the stoppers 75 extend from the pillars 74 toward the center of the circle defined with the base 73 so as to be fitted to the stoppage ditches 57.

Figure 12:
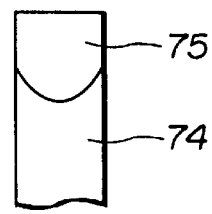
Figure 13:
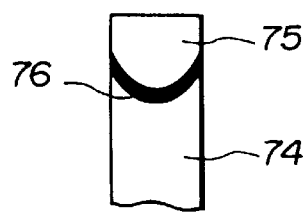
Figure 14:
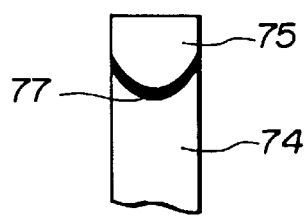

In this embodiment, the bottoms of the stoppers 75 have, as shown in FIG. 12, a circular contour and the tops thereof have a rectangle contour. The stoppers 75 are made of the same material as the piston positioning member 68. The surfaces of the stoppers 75 may be, as shown in FIG. 13, covered with, for example, an elastic material 76 such as rubber or plastic, or, as shown in FIG. 14, coated with a rigid material 77 such as ceramic.

In case the surfaces of the stoppers 75 are covered with the elastic material 76 such as rubber or plastic, when the stoppers 75 touch the rounded surfaces 58 in the piston, occurrence of a touching sound can be prevented. When the surfaces of the stoppers 75 are coated with the rigid material 77 such as ceramic, it is advantageous because the stoppers 75 are hardly abraded despite their touching of the rounded surfaces 58.

Returning to FIG. 8, it is seen that two anti-rotation convex portions 78 are located at the opposite positions under the bottom of the base 73. The anti-rotation convex portions 78 and pillars 74 are opposed to each other above and below the base 73.

Figure 15:
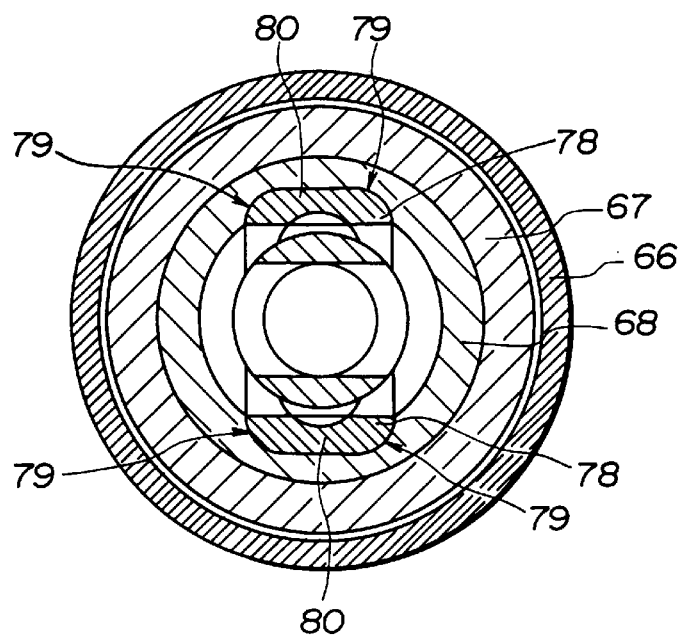

Each of the anti-rotation convex portions 78 has, as shown in the FIG. 15 cross section along line 15—15 of FIG. 8, both ends thereof formed as spherical sections 79 that are spherical. The spherical sections 79 are linked by a curved surface 80.

The cylinder unit 35 comprises, as shown in FIG. 1, three component parts; a cylinder body 81, and an upstream channel 82 and downstream channel 83 which are metallic pipes made of SUS or the like and coupled with the cylinder body 81. The cylinder body 81 is formed with one component part and does not have any projection such as a pin inside. Since the cylinder body 81 is formed with one component part and does not have any projection such as a pin inside, the cylinder body 81 can be cleaned readily during cleaning.

The cylinder body 81 has an upper tapered section 84 in the vicinity of an opening at the upper end thereof. A thread 85 is formed along the outer circumference of the upper part of the cylinder body 81. A collar 86 is formed along the outer circumference of the center part of the cylinder body 81. A cylinder mounting opening 87, in which the cylinder body 81 is mounted is formed in the operation unit 5. For mounting, the cylinder body 81, a plate member 88 is interposed between the collar 86 and operation unit 5, and then the thread 85 formed along the outer circumference of the upper part of the cylinder body 81 is mated with a nut 89. An O-ring 90 is attached to the cylinder body 81 and cylinder mounting opening 87 in order to ensure watertightness and airtightness for the operation unit 5.

Formed on the internal side of the cylinder unit 35 is a cylindrical piston passage 91. In addition, a tapered section 92 shaped like a truncated cone is formed at the lower end of the piston passage 91. The tapered section 92 and slope 64 have the same inclination.

Formed on the lateral side of the cylinder body 81 is a lateral communication path 93 that is a channel having a circular cross section and communicating with the upstream channel 82. A lower communication path 94 that communicates with the downstream channel 83 is formed at the lower end of the cylinder body 81.

Figure 16:
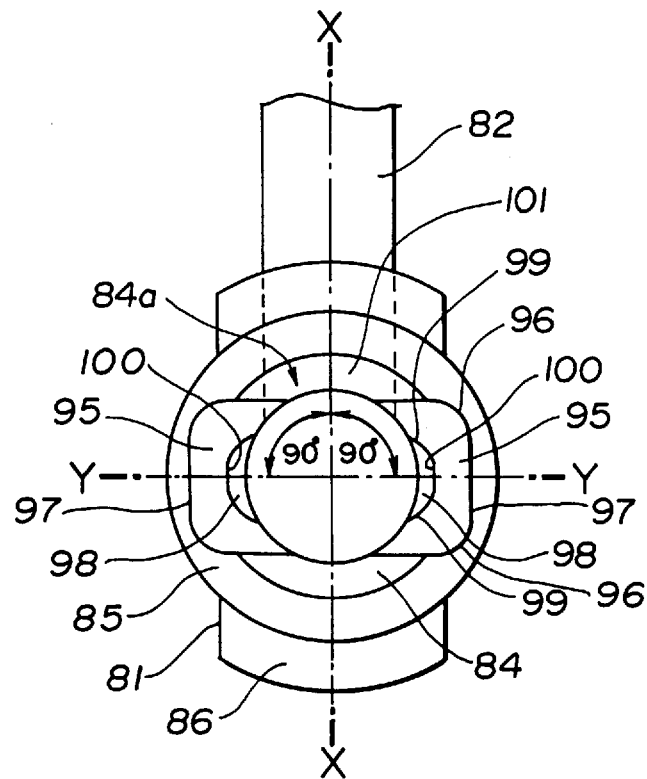

As shown in FIG. 16 in which the cylinder body 81 is viewed from above, concave sections 95 to which the anti-rotation convex sections 78 are fitted are formed in the top of the cylinder body 81. Each of the concave sections 95 has spherical surfaces 96, which are spherical, at both ends thereof. A curved surface 97 for linking the spherical surfaces 96 is interposed between the spherical surfaces 96.

Lower concave sections 98 are formed below the concave sections 95. Each of the lower concave sections 98 has, similarly to each of the concave sections 95, spherical surfaces 99, which are spherical, at both ends thereof. A curved surface 100 for linking the spherical surfaces is interposed between the spherical surfaces 99. Each of the concave sections 95 and a lateral communication port 101 are located at positions that are 90° deviated from each other.

Since the lower concave sections 98 are formed, the concave sections 95 have no horizontal planes on the bottoms. Dirt hardly sticks to the bottoms. Cleaning takes little time. Compared with cleaning efficiency in cleaning of the structure not having the lower concave sections 98, cleaning efficiency improves.

Figure 17:
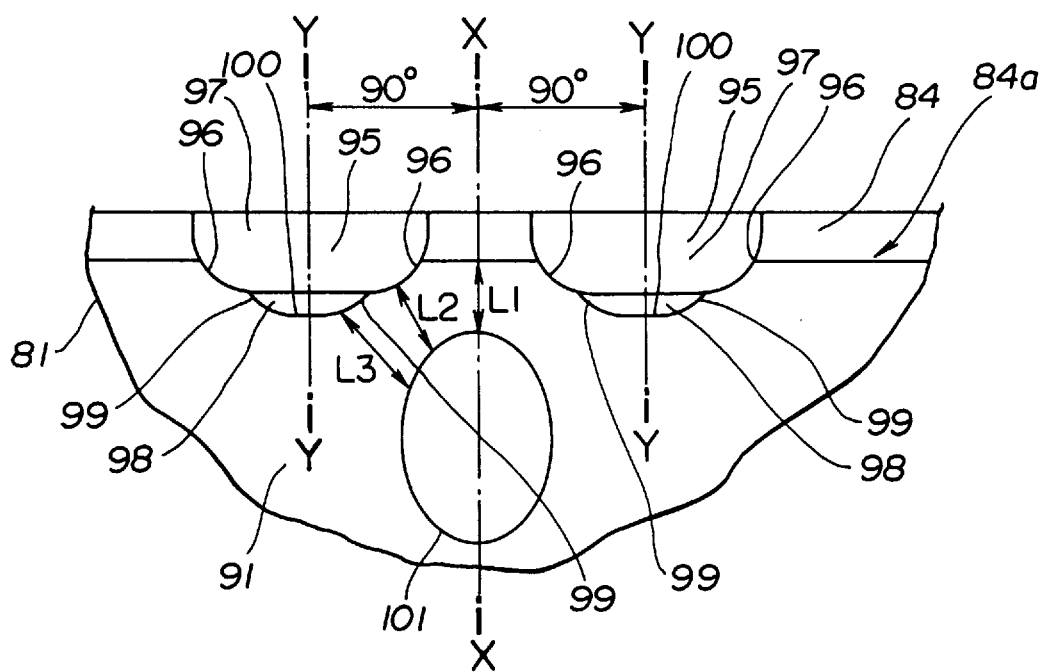

As shown in the FIG. 17 development diagram of the piston passage 91 of the cylinder body 81, the lateral communication port 101 opens below the tapered lower end 84a. A distance L1 from the lateral communication port 101 to the tapered lower end 84a, a distance L2 from the lateral communication port 101 to each concave section 95, and a distance L3 from the lateral communication port 101 to each lower concave section 98 are substantially equal to one another.

Returning to FIG. 1, it is seen that both the upstream channel 82 and downstream channel 83 which are coupled with the cylinder body 81 are fixed to the cylinder body 81 using a solder 102 or adhesive 103.

How to construct the valve unit 36 will be described in conjunction with FIGS. 18 to 20.

Figure 18:
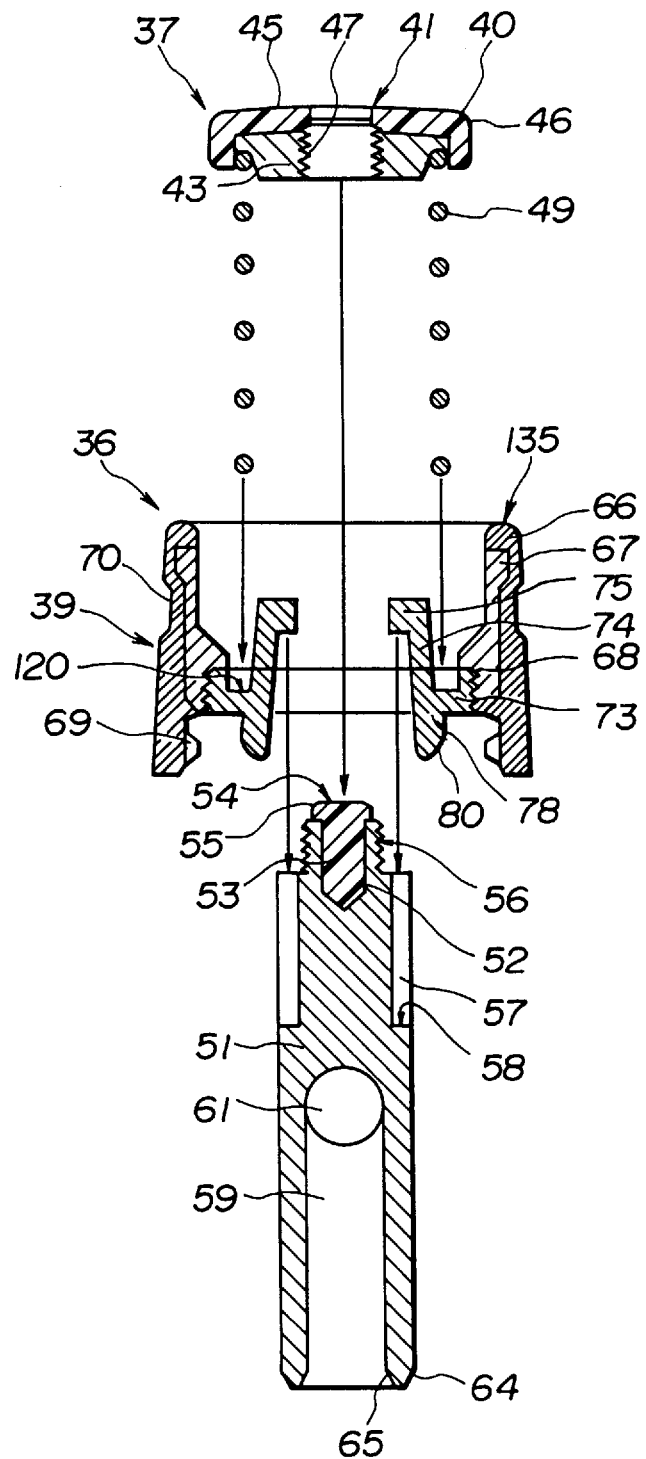

As shown in FIG. 18, the stoppers 75, formed as the peaks of the piston positioning member 68 locked in the mount assembly 39, are fitted into the stoppage ditches 57 in the piston 51. The lower end of the spring 49 is then mounted in a spring ditch 130. The cap 40 is pressed down with the spring 49 compressed. Thereafter, the female thread 47, formed in the metallic member 43 inside the cap 40, is mated with the male thread 56 formed on the upper end of the piston 51. Thus, assembling is completed.

Figure 19:
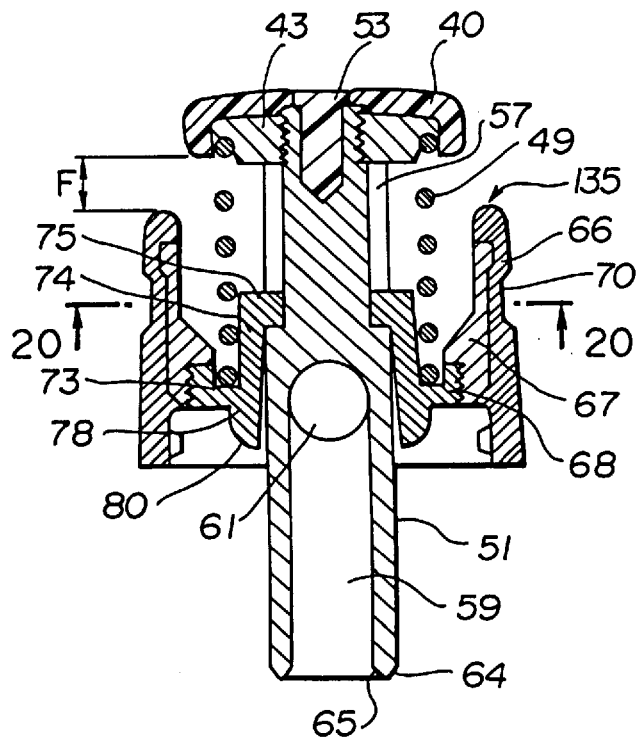

In this state, as shown in FIG. 19, the spring 49 is compressed and the piston 51 is constrained to go up. The stoppers 75 are fitted in the stoppage ditches 57 formed on the lateral side of the piston 51. The stoppers 75 abut the rounded surfaces 58 serving as the bottoms of the stoppage ditches 57. The mounting rubber 66 and piston 51 are thus positioned relative to each other.

Figure 20:
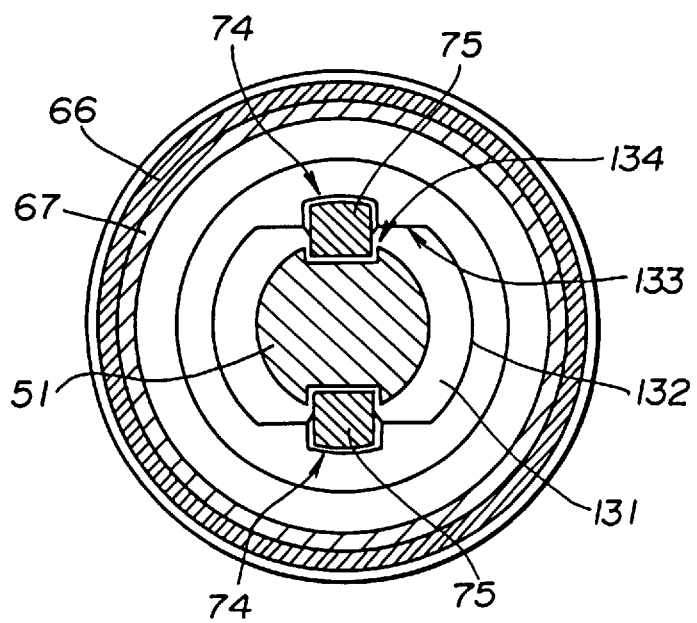

When the valve unit 36 is constructed, as shown in the FIG. 20 cross section along line 20—20 of FIG. 19, the inner circumference 132 of the base 73 borders on a gap 131 and lies in front of the orthogonal channel 61. Since a wider gap than a gap 134 between the piston 51 and each parallel plane 133 is thus preserved, air leaks out reliably in a non-communicating state. The constructed valve unit 36 has a symmetrical shape relative to the center line of the valve unit 36.

Returning to FIG. 19, it is seen that there is a space of a distance F wide between the cap 40 and mounting rubber 66 in the constructed valve unit 36. The width F of the space is set to a value not allowing a test finger, which is used to electrical safety test and which has a distal end of a diameter of 2 mm, to come in.

Referring to FIG. 8, how to mount the constructed valve unit 36 on the cylinder unit 35 will be described.

First, the piston 51 is inserted to the piston passage 91 in the cylinder body 81. The anti-rotation convex sections 78 of the piston positioning member 68 are mounted in the concave sections 95. This restricts the movement in a turning direction of the piston 51 relative to the cylinder 81. As a result, the piston 51 is positioned inside the cylinder. The juts 69 of the mounting rubber 66 are caught by a flange 136 formed along the outer circumference of the upper end of the nut 89. The valve unit 36 will therefore not come off upwardly from the cylinder unit 35. As described previously, the valve unit 36 has a symmetrical shape. When the valve unit 36 is turned a maximum of 90° at the time of mounting on the cylinder unit 35, the anti-rotation convex sections 78 are fitted into the concave sections 95. With a turn of a maximum of 90°, the valve unit 36 can be mounted on the cylinder 81. The mounting work is simple.

Referring to FIG. 1, it is seen that when the valve unit 36 is mounted on the cylinder, the lower end 137 of the orthogonal channel 61 is substantially leveled with the tapered lower end 84a which is the lower end of the upper tapered section 84 of the cylinder body 81. A lower end 113 is located above the lateral communication path 93.

The lower end 137 may be located below the tapered lower end 84a. In this case, a distance from the lower end 137 to the tapered lower end 84a should preferably be equal to or lower than 10% of the diameter of the orthogonal channel 61. Alternatively, the lower end 137 may be located above the tapered lower end 84a. In this case, the distance from the lower end 137 to the tapered lower end 84a should preferably be equal to or lower than 10% of the diameter of the orthogonal channel 61.

In the foregoing case, part of the orthogonal channel 61 is shielded. However, owing to the upper tapered section 84, the openings of the orthogonal channel 61 communicate with the outside of the cylinder body 81 without fail. Although the lower end 137 is located at a position that is lower by a height corresponding to a step of the upper tapered section 84, the height of the valve unit 36 is reduced owing to the upper tapered section 84.

Next, pushing of the valve unit 36 will be described in conjunction with FIGS. 21 to 23.

Figure 21:
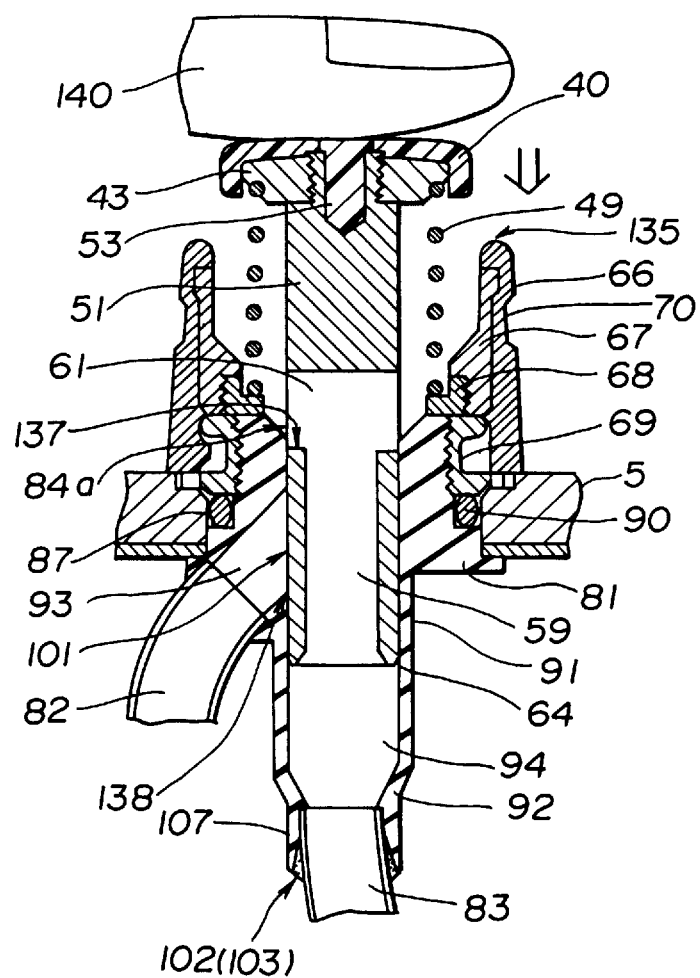

As shown in FIG. 21, in a state in which suction is not carried out, i.e., a state in which the cap 40 is not pressurized by a finger 140, an outer circumferential surface 138 of the piston 51 of the valve unit 36 blocks the lateral communication port 101 of the lateral communication path 93 of the cylinder body 81. The suction channel 28 shown in FIG. 3 is therefore in a non-communicating state, i.e., a state in which the channel is disconnected by the channel switching device 1. The orthogonal channel 61 opens on the outside of the cylinder body 81, and communicates with the space between the cap 40 and the upper end 135 of the mounting rubber 66.

Even when the suction pump 32 shown in FIG. 3 is actuated, therefore, intake air passes through the orthogonal channel 61 to the space between the cap 40 and the upper end 135 of the mounting rubber 66 and then, leaks out to the outside of the valve unit 36. This state is referred to as a suction standby state.

Even if the lower end 137 is located below the tapered lower end 84a (See FIG. 8), as long as the distance from the lower end 137 to the tapered lower end 84a is equal to or lower than 10% of the diameter of the orthogonal channel 61, the non-communicating state can be retained.

Figure 22:
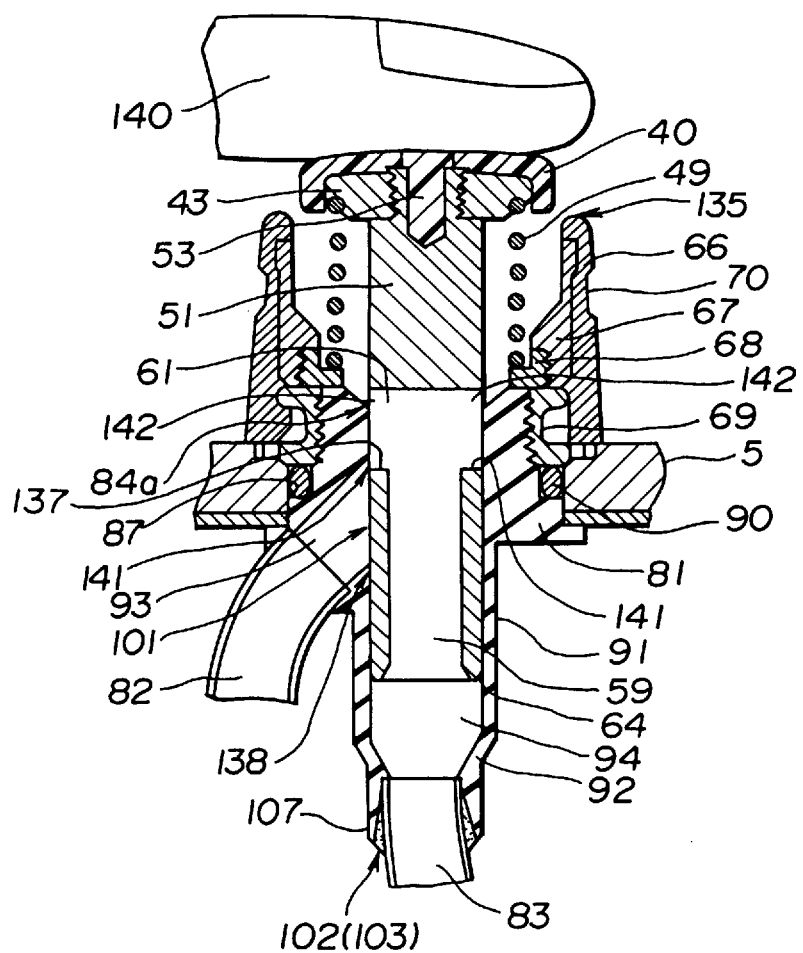

When the valve unit 36 is further pushed, as shown in FIG. 22, a lower opening 141 of the orthogonal channel 61 communicates with the lateral communication port 101. At this time, the upper openings 142 of the orthogonal channel 61 are exposed to the outside of the cylinder body 81 and communicating with the space between the cap 40 and the upper end 135 of the mounting rubber 66. Intake air supplied from the suction pump 32 partly passes through the upper openings 142 to the space between the cap 40 and the upper end 135 of the mounting rubber 66, and then leaks out to the outside of the valve unit 36. Part of the intake air flows into the upstream channel 82 through the lateral communication port 101. As a result, suction can be achieved through a suction port 34 that is formed at the tip of the insertional part 4 and communicate with the upstream channel 82 (See FIG. 3).

Figure 23:
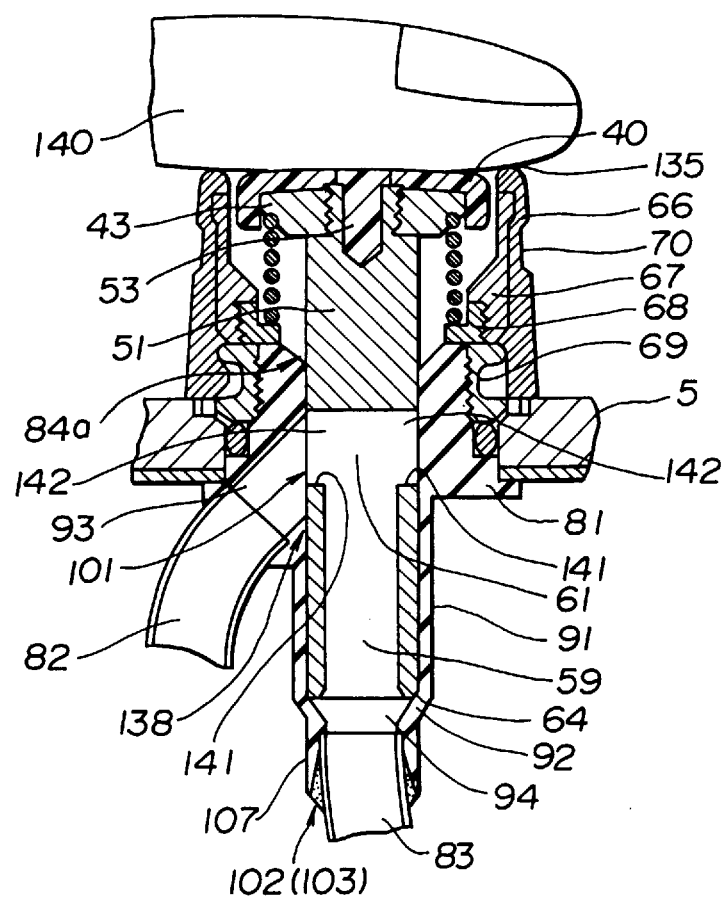

When the valve 36 is further pushed, as shown in FIG. 23, the slope 64 formed in the lower part of the piston 51 abuts the tapered section 92 formed in the lower part of the cylinder body 81. Consequently, the downward movement of the piston 51 is restricted.

In this state, the whole orthogonal channel 61 is enclosed in the piston passage 91. The orthogonal channel 61 therefore, does not open on the outside of the cylinder body 81 at all. Compared with the state shown in FIG. 22 in which part of the orthogonal channel 61 opens on the outside, suction can be achieved reliably.

As shown in FIG. 23, in the state in which the valve unit 36 is fully pushed down, the finger 140 touches the upper end 135 of the mounting rubber 66. The space between the cap 40 and the upper end 135 of the mounting rubber 66 is therefore blocked completely. Although a very small amount of intake air may leak out through the gap between the piston passage 91 and the outer circumferential surface 138 of the piston, the intake air can be shut off reliably. This results in more reliable suction. When the valve 36 is fully pushed, the button assembly 37 and the upper end 135 of the mounting rubber 66 are substantially level with each other.

When the channel switching device 1 is pushed down, as shown in FIG. 3, the channels communicate with each other. Suction can therefore be achieved through the suction port 34 opening at the tip of the insertional part 4.

In the non-communicating state, the outer circumferential surface 138 of the piston blocks the lateral communication port 101. At this time, as described using FIG. 17, the distances L1, L2, and L3 are substantially equal to one another. The concave sections 95 and lower concave sections 98 are formed in the upper end of the cylinder body 81. The piston passage 91 is not formed along the whole circumference of the upper part of the cylinder body 81. Nevertheless, a channel can be blocked reliably. As shown in FIG. 23, even when the piston 51 reaches the lowermost position to enable suction, a channel can be blocked reliably.

Figure 24:
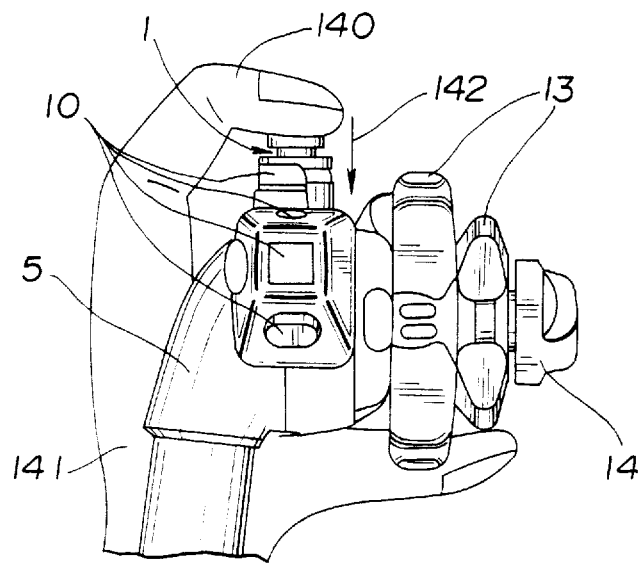
Figure 25:
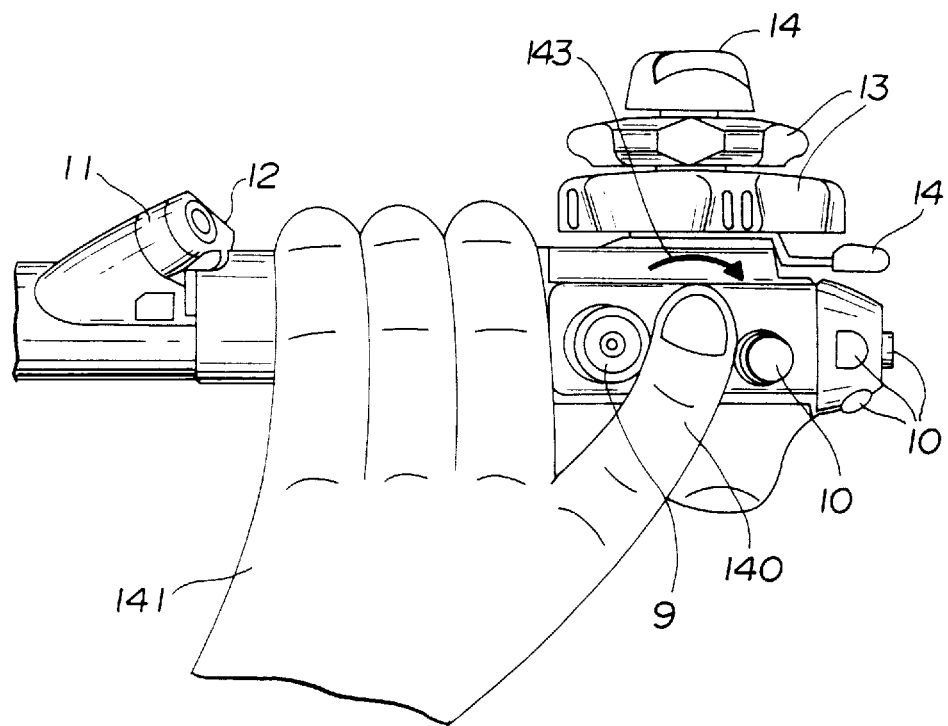

The movement of the finger 140 for pushing down the button assembly 37 of the valve unit 36 will be described below. As shown in FIGS. 24 and 25, the operation unit 5 of the endoscope 2 is held by a left hand 141. When the button assembly 37 of the channel switching device 1 mounted on the operation unit 5 is pushed by the finger 140 of the left hand, the finger 140 is seen making a movement of downward pushing as indicated with an arrow 142 in FIG. 24 when viewed from behind the operation unit 5. When the operation unit 5 is viewed from above, the finger is seen making a movement in a turning direction indicated with an arrow 143 in FIG. 25. In reality, the finger makes a movement that is a combination of the movements indicated with two arrows 142 and 143. That is to say, the movement in a turning direction is added to the downward movement.

At this time, since the female thread 47 formed in the metallic member 43 inside the cap 40 and the male thread 56 of the piston 51, which are mated up, are right-hand threads, a force working on the threads is a force oriented in a direction in which the threads are tightened. Even when the cap 40 is pushed down, the threads will therefore not be loosened (See FIG. 1).

In other words, since the female thread 47 formed in the metallic member 43 inside the cap 40 and the male thread 56 of the piston 51, which are mated up, are right-hand threads, even when the cap 40 is pushed down, the threads will not be loosened. Even if the button assembly 37 is structured so that it can be disassembled and reassembled, no problem occurs in terms of manipulation.

For autoclaving (high-pressure steam sterilization), in general, the conditions of temperature and pressure are about 135° C. and 2 kgf/cm$^2$ at their highest. However, the cap 40 of the valve unit 36 is made of a rigid resin durable to autoclaving, such as, polyether ketone (PEEK) or polysulfone (PSU). The thermal alteration temperatures of the materials durable to autoclaving are higher than a maximum temperature of 135° C. of autoclaving. There is therefore no possibility that the resins of polyether ketone (PEEK) and polysulfone (PSU) may crack and alter.

According to this embodiment, when the valve unit 36 is detached from the endoscope 2 for autoclaving, the valve unit 36 will not be damaged due to autoclaving. Even when the autoclaved valve unit 36 is put to use though it is not yet cooled down, an operator will not perceive heat very much but can manipulate the endoscope 2 as he/she intends.

The valve unit 36 to be included in the channel switching device in the aforesaid embodiment may be structured to be capable of autoclaving as mentioned below.

To be more specific, in a variant of the channel switching device of the aforesaid embodiment that is capable of autoclaving, the button assembly 37 constituting the valve unit 36 is made of a resin durable to autoclaving; such as, polyether ketone (PEEK) or polysulfone (PSU).

As described previously, there is no possibility that the resins of polyether ketone (PEEK) and polysulfone (PSU) may crack or alter under the conditions for autoclaving. The valve unit 36 will therefore not be damaged due to autoclaving. Manipulation in a state in which the valve unit 36 is not yet cooled down can be achieved more easily.

In this variant permitting autoclaving, the insert 67, piston positioning member 68, piston 51, and metallic member 43, which are metallic component parts, are made of a metal such as SUS or aluminum that does not corrode or alter due to autoclaving. Adhesives used for the valve unit 36 shall be those resistive to autoclaving, for example, epoxy adhesives.

As described in conjunction with the embodiment, the gaps between the cap 40 and metallic member 43, and between the index 53 and piston 51 are filled with the adhesives without any clearance. Even after autoclaving, it will not occur that air remaining in the gaps between the piston 51 and index 53 or between the cap 40 and metallic member 43 expands. Peeling-off or cracking of an adhesive will therefore not occur. Moreover, the mounting rubber 66 is made of silicon rubber durable to autoclaving.

In the variant permitting autoclaving, not only the valve unit 36 to be coupled with the suction channel 28 but also the aeration/perfusion valve 9, which is shown in FIG. 2, to be coupled with the channel switching device, are made of a material resistive to autoclaving. In the variant permitting autoclaving, since both the valve unit 36 and aeration/perfusion valve 9 are made of a material resistive to autoclaving, the valves in the endoscope can be sterilized at one time. This results in simplified sterilization.

Next, the second embodiment of the present invention will be described. The second embodiment is substantially identical to the first embodiment. Only different components will be described. Components identical to those in the first embodiment will be assigned the same reference numerals. The description of the components will be omitted.

In the second embodiment, all the structures except the button assembly 37, piston positioning member 68, and cylinder body 81 are identical to those in the first embodiment.

Figure 26:
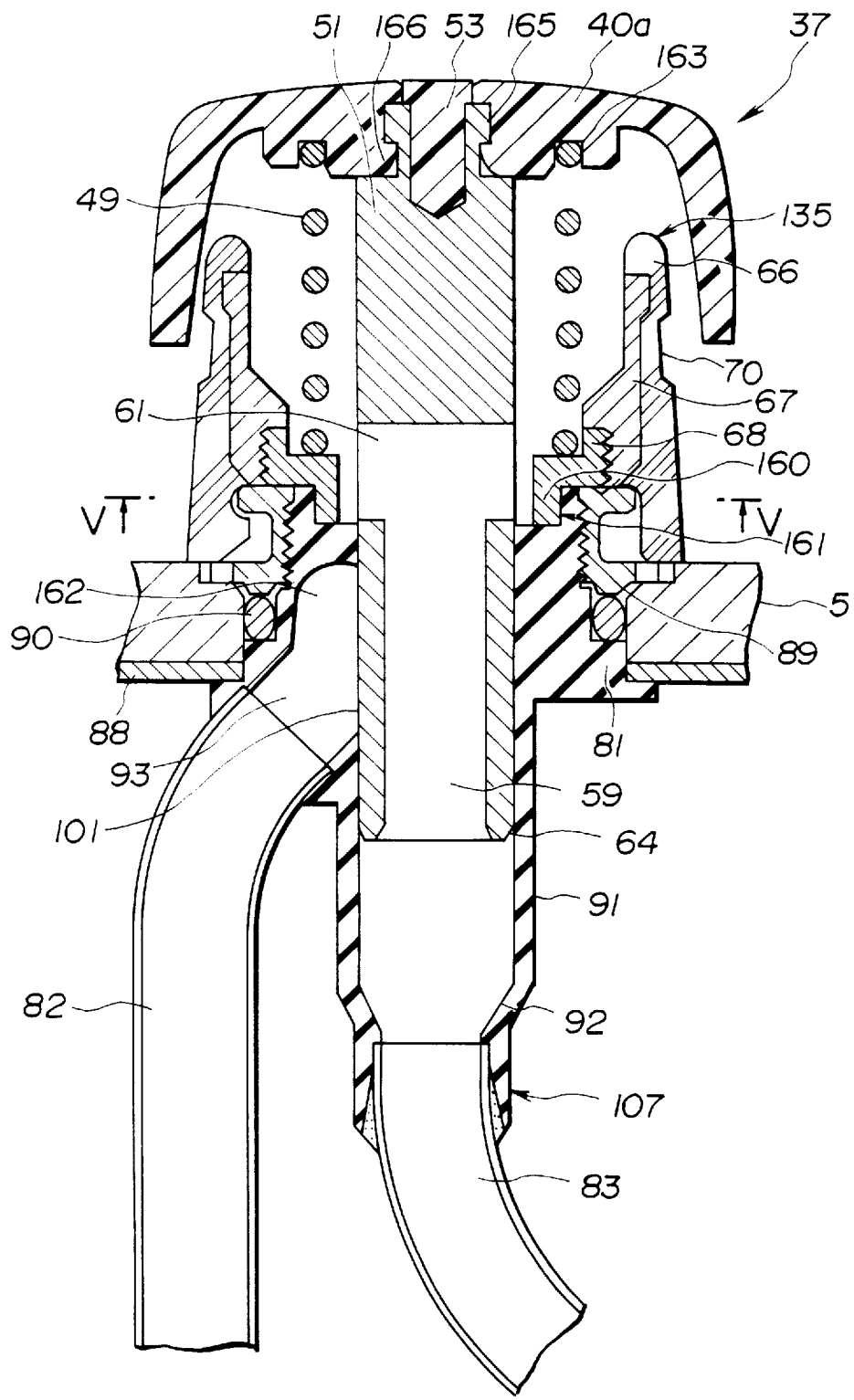
FIGS. 26 to 28 relate to the second embodiment.
Figure 27:
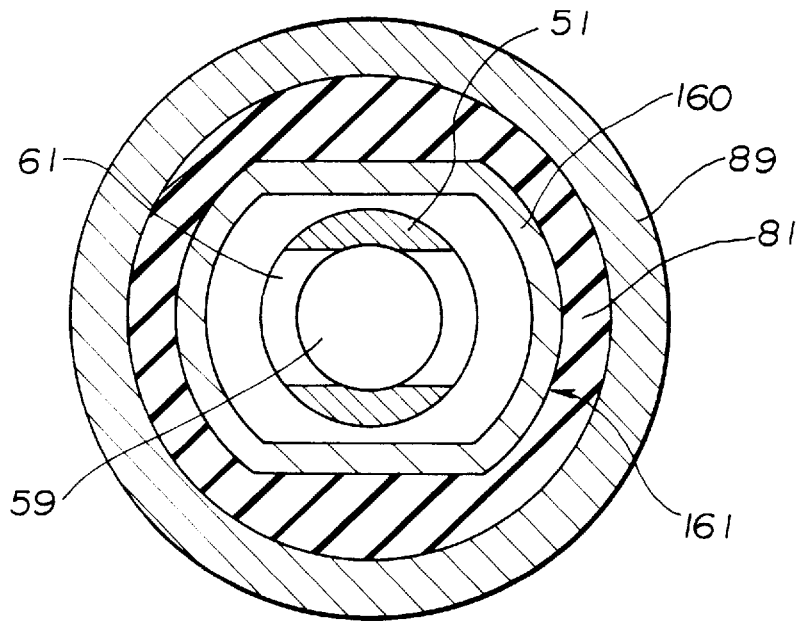

In this embodiment, as shown in FIG. 26 and the FIG. 27 cross section along line 27—27 of FIG. 26, an anti-rotation part 160 having an elliptic cross section is formed as the lower part of the piston positioning member. A mounting hole 161, having the same cross section as the anti-rotation part 160, is formed in the upper end of the cylinder body 81.

A space 162 is preserved above the lateral communication port 101 of the cylinder body 81. A cap 40a of this embodiment has an appearance of a truncated cone. The lateral side of the cap 40a is inclined or sloped. There is no metallic member inside the cap 40a. The cap 40 is molded as a united body using a rigid resin such as PSU or PEEK. A locking ditch 163, for locking the spring 49, is bored directly in the cap 40a.

The button assembly 37 and piston assembly 38 are detachably fixed to each other with a snap fit with which a claw 166 of the cap is hooked on to a jut 165 formed at the apex of the piston 51.

Figure 28:
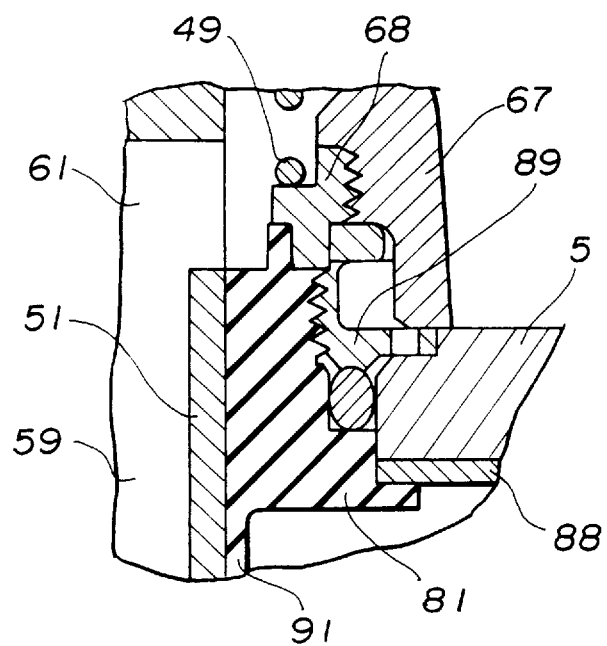
Figure 29:
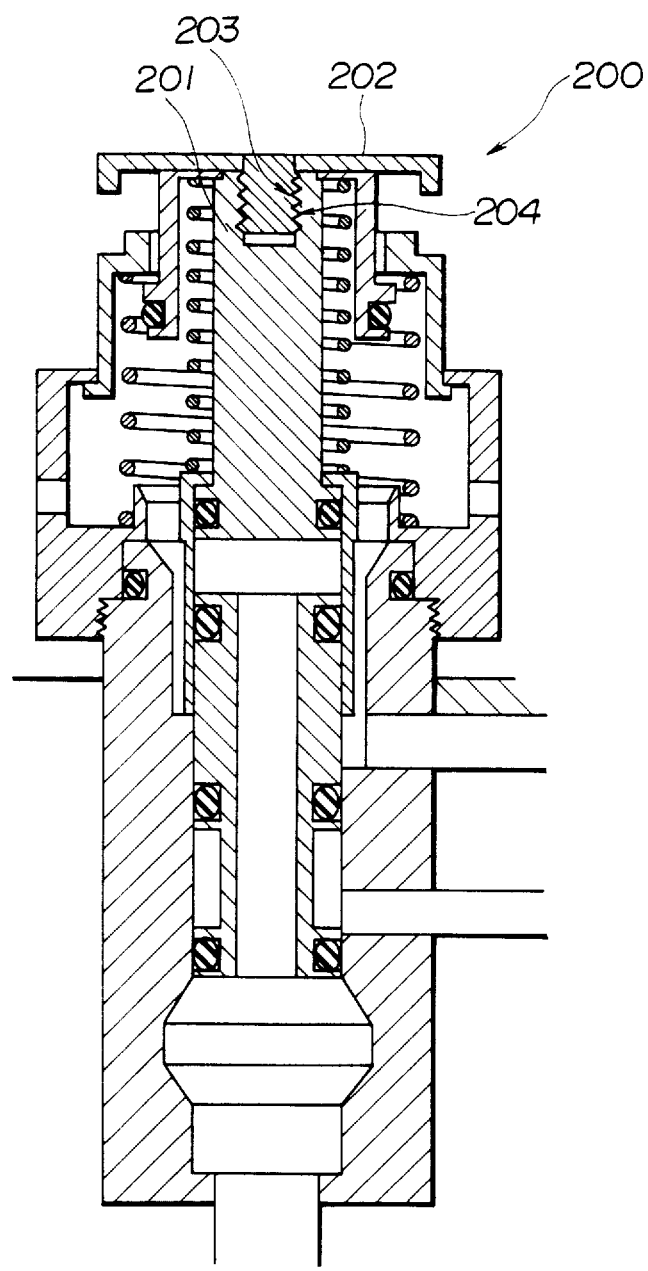
FIG. 29 is a sectional view showing the structure of a channel switching device in accordance with a prior art.

The mounting hole 161 may be, as shown in FIG. 28, preserved between the cylinder body 81 and nut 89.

The other components are identical to those in the first embodiment.

In the second embodiment, the anti-rotation part 160 is fitted into the mounting hole 161. Thus, the piston 51 and cylinder body 81 are positioned relative to each other.

For collecting a solid substance such as a polyp by performing suction, since the space 162 is preserved in the vicinity of the lateral communication port 101 of the cylinder body 81, the solid substance such as a polyp can be collected smoothly but will not be caught between the lateral communication port 101 and orthogonal channel 61.

For suction, when the cap 40a is pushed down, the cap 40a abuts the upper end 135 of the mounting rubber. Even if a leakage of intake air occurs between the cylinder body 81 and piston 51, the air leakage can be shut off completely.

Consequently, when the cap 40a abuts the upper end 135 of the mounting rubber, suction is achieved more reliably. Since the cap 40a and piston assembly 38 are fixed to each other with a snap fit, they can be detached from each other readily.

As mentioned above, in the second embodiment, there is no metallic member inside the cap 40a. The cap 40a is molded as a united body using a rigid resin durable to autoclaving, such as, polyether ketone (PEEK) or polysulfone (PSU). Similarly to that in the first embodiment, the valve unit 36 will not be damaged due to autoclaving. Even when the autoclaved valve unit 36 is put to use though it is not yet cooled down, an operator will not perceive heat very much but can manipulate the endoscope as he/she intends.

In the present invention, it will be apparent that a wide range of embodiments can be constructed on the basis of the invention without a departure from the spirit and scope of the invention. This invention is limited to the appended claims but not restricted to any specific embodiments.

What is claimed is:

1. An endoscope, comprising:
   channels lying through said endoscope; and
   a channel switching means for switching communicating states of said channels, wherein said channel switching means is located between said channels, said channel switching device comprising a cylinder unit and a valve unit, wherein said valve unit is detachable from said cylinder unit, said valve unit is comprised of a plurality of members such that all members of said plurality of members comprising said valve unit are made of a material which is both durable to disinfection, when exposed to a disinfectant solution, and durable to autoclaving, and said valve unit has an outer surface made of a material other than a metal when mounted on said cylinder unit.

2. The endoscope according to claim 1, wherein said outer surface of said valve unit is made of a resin or elastic body.

3. The endoscope according to claim 1, wherein said outer surface of said valve unit is made of a material having a property of electrical insulation.

4. The endoscope according to claim 1, wherein said valve unit includes a member made of a material other than a metal and a member made of a metal, and wherein when said valve unit is mounted on said cylinder unit, said member made of a metal lies in a place other than said outer surface of said valve unit.

5. The endoscope according to claim 3, wherein an opening in said outer surface of said valve unit has a clearance equal to or smaller than 2 mm.

6. The endoscope according to claim 2, wherein said resin is polysulfone or polyether ketone.

7. The endoscope according to claim 2, wherein said elastic body is silicon rubber.

8. The endoscope according to claim 2, wherein said valve unit includes a member made of a material other than a metal and a member made of a metal, and wherein when said valve unit is mounted on said cylinder unit, said member made of a metal lies in a place other than said outer surface of said valve unit.

9. The endoscope according to claim 3, wherein said valve unit includes a member made of a material other than a metal and a member made of a metal, and wherein when said valve unit is mounted on said cylinder unit, said member made of a metal lies in a place other than said outer surface of said valve unit.

* * * * *